United States Patent
Pringle et al.

(10) Patent No.: US 10,388,505 B2
(45) Date of Patent: Aug. 20, 2019

(54) MONITORING ION MOBILITY SPECTROMETRY ENVIRONMENT FOR IMPROVED COLLISION CROSS SECTION ACCURACY AND PRECISION

(71) Applicant: Micromass UK Limited, Wilmslow (GB)

(72) Inventors: Steven Derek Pringle, Darwen (GB); Farnoush Salarzaei, Altrincham (GB); Nicholas Tomczyk, Altrincham (GB); Jason Lee Wildgoose, Stockport (GB)

(73) Assignee: Micromass UK Limited, Wilmslow (GB)

( * ) Notice: Subject to any disclaimer, the term of this patent is extended or adjusted under 35 U.S.C. 154(b) by 0 days.

(21) Appl. No.: 15/317,017

(22) PCT Filed: Jun. 10, 2015

(86) PCT No.: PCT/GB2015/000168
§ 371 (c)(1),
(2) Date: Dec. 7, 2016

(87) PCT Pub. No.: WO2015/189540
PCT Pub. Date: Dec. 17, 2015

(65) Prior Publication Data
US 2017/0117129 A1     Apr. 27, 2017

(30) Foreign Application Priority Data

Jun. 11, 2014 (GB) .................................. 1410369.1
Aug. 20, 2014 (EP) .................................. 14181504
Aug. 20, 2014 (GB) .................................. 1414753.2

(51) Int. Cl.
*H01J 49/24* (2006.01)
*G01N 30/26* (2006.01)
(Continued)

(52) U.S. Cl.
CPC ............ *H01J 49/24* (2013.01); *G01N 27/622* (2013.01); *G01N 30/7233* (2013.01);
(Continued)

(58) Field of Classification Search
CPC ...... G01N 27/622; G01N 30/26; G01N 30/30; G01N 30/54; H01J 49/004; H01J 49/0031; H01J 49/0422; H01J 49/26
(Continued)

(56) References Cited

U.S. PATENT DOCUMENTS 5,552,600 A   9/1996  Davies et al.
5,736,739 A   4/1998  Uber et al.
(Continued)

FOREIGN PATENT DOCUMENTS

EP   1562040 A2   8/2005
EP   2 613 140    7/2013
(Continued)

OTHER PUBLICATIONS

Owlstone, "A Comparison of the 3 Main Forms of Ion Mobility Spectrometry", www.ultrafaims.com, 2014.
(Continued)

*Primary Examiner* — David A Vanore

(57) ABSTRACT

A mass spectrometer is disclosed comprising an ion mobility separator for separating ions according to their ion mobility, one or more first devices or stages arranged upstream of the ion mobility separator and a control system. The control system is arranged and adapted to monitor directly or indirectly the operating environment within the ion mobility separator, and to control the operating environment within the ion mobility separator based on the monitoring by controlling one or more gas flows to or within one or more of the one or more first devices or stages.

18 Claims, 6 Drawing Sheets

(51) Int. Cl.
*G01N 27/62* (2006.01)
*H01J 49/00* (2006.01)
*G01N 30/72* (2006.01)

(52) U.S. Cl.
CPC ........ *H01J 49/004* (2013.01); *H01J 49/0009* (2013.01); *H01J 49/0027* (2013.01); *H01J 49/0045* (2013.01)

(58) Field of Classification Search
USPC ....... 250/281, 282, 288, 287, 286, 291, 289, 250/396 R
See application file for complete search history.

(56) References Cited

U.S. PATENT DOCUMENTS

| | | | |
|---|---|---|---|
| 5,796,099 A | 8/1998 | Jackson | |
| 6,177,001 B1* | 1/2001 | Meyer | G01N 27/4175 204/427 |
| 6,803,567 B2 | 10/2004 | Leonhardt et al. | |
| 6,967,325 B2 | 11/2005 | Smith et al. | |
| 7,112,788 B2 | 9/2006 | Guevremont et al. | |
| 7,388,197 B2 | 6/2008 | McLean et al. | |
| 7,579,589 B2* | 8/2009 | Miller | G01N 27/624 250/281 |
| 7,608,818 B2 | 10/2009 | Miller et al. | |
| 7,919,747 B2 | 4/2011 | Green et al. | |
| 8,153,960 B2* | 4/2012 | Giles | H01J 49/427 250/281 |
| 8,173,959 B1 | 5/2012 | Boumsellek et al. | |
| 8,426,802 B2 | 4/2013 | Giles et al. | |
| 8,610,054 B2* | 12/2013 | Giles | G01N 27/624 250/282 |
| 8,624,179 B2* | 1/2014 | Chen | H01J 49/0072 250/281 |
| 9,024,255 B2* | 5/2015 | Osgood | C07B 63/00 250/281 |
| 9,089,279 B2* | 7/2015 | Wang | A61B 5/082 |
| 9,093,254 B2 | 7/2015 | Rand et al. | |
| 9,305,762 B2 | 4/2016 | Covey et al. | |
| 9,400,261 B2* | 7/2016 | Black | G01N 27/624 |
| 9,523,658 B2* | 12/2016 | Giles | G01N 27/622 |
| 9,625,358 B2* | 4/2017 | Murthy | G01N 1/2202 |
| 2002/0014586 A1* | 2/2002 | Clemmer | G01N 27/622 250/287 |
| 2003/0116705 A1 | 6/2003 | Kanik et al. | |
| 2007/0158543 A1 | 7/2007 | Clowers et al. | |
| 2010/0282966 A1* | 11/2010 | Schneider | G01N 27/622 250/282 |
| 2011/0183431 A1 | 7/2011 | Covey et al. | |
| 2012/0326023 A1 | 12/2012 | Kozole et al. | |
| 2013/0168548 A1 | 7/2013 | Wang et al. | |
| 2014/0290340 A1* | 10/2014 | Murthy | G01N 1/2226 73/31.07 |

FOREIGN PATENT DOCUMENTS

| | | |
|---|---|---|
| EP | 2613140 A1 | 7/2013 |
| EP | 2634556 A1 | 9/2013 |
| WO | 2006/119167 A1 | 11/2006 |
| WO | 2008/005283 A2 | 1/2008 |
| WO | 2010/125357 A2 | 11/2010 |
| WO | 2011/020034 A1 | 2/2011 |
| WO | 2013/080044 A2 | 6/2013 |

OTHER PUBLICATIONS

Examination Report for GB Patent Application No. GB1510080.3 dated Oct. 17, 2017.
Owlstone Inc., 2014, "A Comparison of the 3 Main Forms of Ion Mobility Spectrometry", Owlstonenanotech.com, [online], available from:http://web.archive.org/web/20170116112118/http://www.owlstonenanotech.com/sites/default/files/ultrafaims/UMC0044-At-A-Glance-Guide-Main-Forms-IMS.pdf, 2014.
Himmelsbach, M., "10 years of MS instrumentaldevelopments—Impact on LC-MS/MS in clinical chemistry", Journal of Chromatography B, vol. 883-884, pp. 3-17, 2012.
Examination Report for GB Patent Application No. GB1510080.3 dated Jun. 27, 2018.
Combined Search and Examination Report for GB Patent Application No. GB1812676.3 dated Oct. 19, 2018.

* cited by examiner

MONITORING ION MOBILITY SPECTROMETRY ENVIRONMENT FOR IMPROVED COLLISION CROSS SECTION ACCURACY AND PRECISION

CROSS-REFERENCE TO RELATED APPLICATIONS

This application represents the U.S. National Phase of International Application number PCT/GB2015/000168 entitled "Monitoring Ion Mobility Spectrometry Environment for Improved Collision Cross Section Accuracy and Precision" filed 10 Jun. 2015, which claims priority from and the benefit of United Kingdom patent application No. 1410369.1 filed on 11 Jun. 2014, United Kingdom patent application No. 1414753.2 filed on 20 Aug. 2014 and European patent application No. 14181504.3 filed on 20 Aug. 2014. The entire contents of these applications are incorporated herein by reference.

FIELD OF THE INVENTION

The present invention relates generally to mass spectrometry and in particular to ion mobility-mass spectrometry.

BACKGROUND

Ion Mobility Separation or Spectrometry ("IMS") is a well established analytical technique whereby ions are separated according to their ion mobility by subjecting the ions to a weak electric field in the presence of a buffer gas. The ions experience a force in one direction due to the electric field and an effective force in the opposite direction due to collisions with the buffer gas.

At low electric fields, the ion mobility of a given ion, K, can be calculated approximately with the equation:

$$K = \frac{3}{16}\sqrt{\frac{2\pi}{\mu kT}}\frac{Q}{n\sigma} \quad (1)$$

wherein Q is the ion charge, n is the buffer gas number density, p is the reduced mass of the ion and the buffer gas molecules, k is Boltzmann constant, T is the buffer gas temperature and a is the collision cross section ("CCS") of the ion.

When coupling an ion mobility separator to a mass spectrometer or filter ("MS") and/or other analytical devices, it is generally preferable to locate the ion mobility separator between the ion source and the mass spectrometer. This is particularly true when using an ion source that operates at or close to atmospheric pressure, as the operating pressures of typical ion mobility separators fall between atmospheric pressure and the operating pressure of many mass spectrometers.

While this approach is advantageous, e.g. from a cost perspective, it can lead to problems in the accuracy and precision of ion mobility and/or collision cross section measurements, since variations in the ambient (external) or ion source environment can directly influence the internal environment of the ion mobility separator. For example, changes in the ambient environment due to liquid chromatography ("LC") gradient changes, changes in sample or matrix flow rates, and changes in source gas flows rates can all affect the internal ion mobility separator environment.

These effects are typically avoided or reduced by introducing one or more differential pumping stages between the ion source and the ion mobility separator, and re-filling the ion mobility separator with a buffer gas. However, this adds additional cost and complexity to the system.

US 2002/0014586 (Clemmer) discloses with relation to FIG. 5 an IMS arrangement in which a buffer gas is regulated by buffer gas source 46 and a pump 80.

WO 2013/080044 (Hart) discloses a FAIMS system in which temperature and pressure sensors are used to monitor the FAIMS core. Pressure correction is achieved by adjusting the FAIMS scan parameters based on measurements from these sensors.

US 2005/0092918 (Smith) discloses an IMS arrangement in which a buffer gas supplied via lines is regulated using a pressure sensor and a flow regulator.

WO 2010/125357 (Giles) discloses a differential mobility spectrometry (DMS) device arranged in a pressured controlled vacuum chamber.

US 2011/0183431 (Covey) discloses a differential mobility spectrometry (DMS) device arranged in a temperature regulated vacuum chamber.

EP-1562040 (Guevremont) discloses a FAIMS device having a temperature sensor and a temperature controller.

U.S. Pat. No. 5,796,099 (Jackson) discloses an ion mobility spectrometer whose calibration is corrected based on the operating pressure and temperature.

U.S. Pat. No. 5,736,739 (Uber) discloses an IMS device having flow sensors and flow adjustment valves.

EP-2613140 (Sato) discloses an IMS device having a mass flow controller.

It is desired to provide an improved mass spectrometer and an improved method of mass spectrometry.

SUMMARY

According to an aspect there is provided a mass spectrometer comprising:
an ion mobility separator for separating ions according to their ion mobility;
one or more first devices or stages arranged upstream of the ion mobility separator; and
a control system arranged and adapted:
(i) to monitor directly or indirectly the operating environment within the ion mobility separator; and
(ii) to control the operating environment within the ion mobility separator based on the monitoring by controlling one or more gas flows to or within one or more of the one or more first devices or stages.

An embodiment relates to a mass spectrometer comprising an ion mobility separator and one or more first devices or stages arranged upstream of the ion mobility separator. The operating environment (e.g. gas composition and/or pressure) within the ion mobility separator is monitored. The monitoring is used to control the operating environment (e.g. gas composition and/or pressure) within the ion mobility separator by controlling one or more gas flows to or within one or more of the one or more upstream first devices or stages, e.g. using a feedback loop.

The various embodiments are in contrast with known arrangements, such as the arrangement disclosed in US 2002/0014586 (Clemmer) wherein the buffer gas within a drift tube is regulated by a buffer gas source and a pump that are connected directly to the drift tube. In contrast, the approach according to various embodiments is to monitor the operating environment within the ion mobility spectrometer or separator but then to control instead the gas flows within one or more upstream devices—i.e. according to the various embodiments the operating environment within the ion mobility spectrometer or separator is controlled indirectly in contrast to the approach disclosed in US 2002/0014586 (Clemmer) wherein the operating environment within an ion mobility spectrometer or separator is controlled directly.

The various embodiments are particularly advantageous, e.g. in terms of simplicity and cost, as it is possible to obtain accurate measurements, e.g. by ensuring a stable operating environment within the ion mobility separator without necessarily having to isolate the ion mobility separator from the upstream stages of the mass spectrometer (for example, according to an embodiment without necessarily having to provide one or more differential pumping stages between the upstream stages and the ion mobility separator, and according to another embodiment without having to re-fill the ion mobility separator with a buffer gas).

Various embodiments therefore provide an improved mass spectrometer and an improved method of mass spectrometry.

In an embodiment, the control system is arranged and adapted to control the operating environment within the ion mobility separator so as to maintain a substantially stable operating environment within the ion mobility separator.

In an embodiment, the control system is arranged and adapted to control the operating environment within the ion mobility separator so as to maintain a substantially stable operating environment within the ion mobility separator when the operating environment within or of one or more of the one or more first devices or stages changes or varies.

In an embodiment, the control system is arranged and adapted to control the operating environment within the ion mobility separator so as to avoid or reduce changes or variations in the operating environment within the ion mobility separator that would otherwise occur due to changes or variations in the operating environment within or of one or more of the one or more first devices or stages.

According to another aspect there is provided a mass spectrometer comprising:

an ion mobility separator for separating ions according to their ion mobility;

one or more first devices or stages arranged upstream of the ion mobility separator; and a control system arranged and adapted:

(i) to monitor directly or indirectly the operating environment within the ion mobility separator; and (ii) to correct one or more measurements made using the mass spectrometer based on the monitoring when the operating environment within the ion mobility separator changes or varies due to changes or variations in the operating environment within or of one or more of the one or more first devices or stages.

An embodiment relates to a mass spectrometer comprising an ion mobility separator and one or more first devices or stages arranged upstream of the ion mobility separator. The operating environment (e.g. gas composition and/or pressure) within the ion mobility separator is monitored. The monitoring may be used to correct measurements taken using the ion mobility separator which depend on the (varying) operating environment of one or more upstream first devices or stages.

The various embodiments are particularly advantageous, e.g. in terms of simplicity and cost, as it is possible to obtain accurate measurements, e.g. by correcting measurements for errors caused by any variation in the operating environment, without necessarily having to isolate the ion mobility separator from the upstream stages of the mass spectrometer (e.g. according to an embodiment without necessarily providing one or more differential pumping stages between the upstream stages and the ion mobility separator, and in another embodiment without re-filling the ion mobility separator with a buffer gas).

Various embodiments therefore provide an improved mass spectrometer and an improved method of mass spectrometry.

In an embodiment, the ion mobility separator is coupled to the one or more first devices or stages such that the operating environment within the ion mobility separator depends on the operating environment within or of one or more of the one or more first devices or stages.

In an embodiment, the ion mobility separator is coupled to the one or more first devices or stages such that the composition of one or more gases within the ion mobility separator depends on the operating environment within or of the one or more first devices or stages, and in an embodiment such that the composition of one or more gases within the ion mobility separator substantially depends on the composition of one or more gases within or at the one or more first devices or stages.

In an embodiment, the ion mobility separator is coupled to the one or more first devices or stages such that the pressure within the ion mobility separator substantially depends on the operating environment within or of the one or more first devices or stages, and in an embodiment such that the pressure within the ion mobility separator substantially depends on the pressure within the one or more first devices or stages.

In an embodiment, the ion mobility separator is coupled to the one or more first devices or stages such that the ion mobility separator is provided or filled with gas (at least partially) from the one or more first devices or stages.

In an embodiment, the control system is arranged and adapted to monitor directly or indirectly the operating environment within the ion mobility separator by monitoring the composition of one or more gases.

In an embodiment, the control system is arranged and adapted to monitor directly or indirectly the operating environment within the ion mobility separator by monitoring one or more pressures.

In an embodiment, the control system is arranged and adapted to monitor directly or indirectly the operating environment within the ion mobility separator by monitoring a total or absolute pressure.

In an embodiment, the control system is arranged and adapted to monitor directly or indirectly the operating environment within the ion mobility separator by monitoring a plurality of partial pressures.

In an embodiment, the control system is arranged and adapted to monitor indirectly the operating environment within the ion mobility separator:

by directly monitoring an operating environment within or of one or more first devices or stages arranged upstream of the ion mobility separator; and/or by directly monitoring an operating environment within or of one or more second devices or stages arranged downstream of the ion mobility separator; and/or by directly monitoring an operating environment within or of one or more chambers coupled to the ion mobility separator.

In an embodiment, the one or more first devices or stages comprise an ion source.

In an embodiment, the ion source comprises an atmospheric ion source.

In an embodiment, the one or more first devices or stages comprises a liquid chromatography device optionally coupled to the ion source. In an embodiment, the liquid chromatography device is upstream of the ion source.

In an embodiment, the one or more first devices or stages comprises one or more transfer regions optionally downstream of the ion source.

In an embodiment, the one or more first devices or stages comprises one or more traps or trap regions optionally downstream of the ion source and optionally downstream of the one or more transfer regions.

In an embodiment, the pressure within the ion mobility separator is less than the pressure within or at the one or more first devices or stages.

In an embodiment, the mass spectrometer further comprises one or more second devices or stages arranged downstream of the ion mobility separator.

In an embodiment, the one or more second devices or stages comprise a mass analyser.

In an embodiment, the pressure within the ion mobility separator is greater than the pressure within or at the one or more second devices or stages.

In an embodiment:
the ion mobility separator comprises a trap region and a separation or drift region; and
the control system is arranged and adapted to monitor directly or indirectly the operating environment within the ion mobility separator by monitoring the trap region and/or the separation or drift region.

In an embodiment, the control system is arranged and adapted to monitor directly or indirectly the operating environment within the ion mobility separator: (i) substantially continuously; (ii) non-continuously; and/or (ii) periodically.

In an embodiment, the control system is arranged and adapted to control the operating environment within the ion mobility separator by controlling the composition of one or more gases within the ion mobility separator.

In an embodiment, the control system is arranged and adapted to control the operating environment within the ion mobility separator by controlling one or more pressures within the ion mobility separator.

In an embodiment, the control system is arranged and adapted:
to control the total or absolute pressure within the ion mobility separator; and/or
to control a plurality of partial pressures within the ion mobility separator.

In an embodiment, the control system is arranged and adapted to correct one or more measurements of drift time and/or collision cross section based on the monitoring.

According to an aspect there is provided a method of mass spectrometry comprising:
providing an ion mobility separator for separating ions according to their ion mobility;
providing one or more first devices or stages upstream of the ion mobility separator;
monitoring directly or indirectly the operating environment within the ion mobility separator; and
controlling the operating environment within the ion mobility separator based on the monitoring by controlling one or more gas flows to or within one or more of the one or more first devices or stages.

According to an aspect there is provided a method of mass spectrometry comprising:
providing an ion mobility separator for separating ions according to their ion mobility;
providing one or more first devices or stages upstream of the ion mobility separator;
monitoring directly or indirectly the operating environment within the ion mobility separator; and
correcting one or more measurements made using the mass spectrometer based on the monitoring when the operating environment within the ion mobility separator changes or varies due to changes or variations in the operating environment within or of one or more of the one or more first devices or stages.

According to an aspect there is provided a mass spectrometer comprising:
a separation device arranged and adapted to separate ions according to a first physico-chemical property;
one or more first devices or stages arranged upstream of the separation device; and
a control system arranged and adapted:
(i) to monitor directly or indirectly the operating environment within the separation device; and
(ii) to control the operating environment within the separation device based on the monitoring by controlling one or more gas flows to or within one or more of the one or more first devices or stages.

According to an aspect there is provided a mass spectrometer comprising:
a separation device arranged and adapted to separate ions according to a first physico-chemical property;
one or more first devices or stages arranged upstream of the separation device; and
a control system arranged and adapted:
(i) to monitor directly or indirectly the operating environment within the separation device; and
(ii) to correct one or more measurements made using the mass spectrometer based on the monitoring when the operating environment within the separation device changes or varies due to changes or variations in the operating environment within or of one or more of the one or more first devices or stages.

Other embodiments relate to a mass spectrometer comprising a separation device and one or more first device or stages upstream of the separation device. The separation device may comprise a device which separates ions according to a first physico-chemical property, wherein the degree of separation in an embodiment depends on the operating environment (e.g. gas composition and/or pressure) within the separation device, such as for example an ion mobility separation device.

In an embodiment, the separation device (e.g. ion mobility separator) is coupled to the one or more upstream devices or stages such that the operating environment (e.g. gas composition and/or pressure) within the separation device depends on the operating environment (e.g. gas composition and/or pressure) within or of one or more of (optionally all of) the one or more first devices or stages. Thus, in an embodiment the operating environment (e.g. gas composition and/or pressure) within the separation device is affected by the operating environment (e.g. gas composition and/or pressure) within or of one or more of the upstream stages.

The operating environment (e.g. gas composition and/or pressure) within the separation device may be monitored, and the monitoring may be used to control the operating environment (e.g. gas composition and/or pressure) within the separation device by controlling one or more gas flows to or within one or more of the one or more first devices or stages, e.g. using a feedback loop, and/or to correct measurements taken using the separation device which in an embodiment will depend on the (varying) operating environment.

The various embodiments are particularly advantageous, e.g. in terms of simplicity and cost, as it is possible to obtain accurate measurements, i.e. by ensuring a stable operating environment within the separation device, or by correcting measurements for errors caused by any variation in the operating environment, without having to isolate the separation device from the upstream stages of the mass spectrometer (in an embodiment without providing one or more differential pumping stages between the upstream stages and the separation device, and in an embodiment without re-filling the separation device with a buffer gas).

The various embodiments therefore provide an improved mass spectrometer and an improved method of mass spectrometry.

In an embodiment, the separation device is arranged and adapted such that the degree of separation of ions according to the first physico-chemical property depends on the operating environment within the separation device.

In an embodiment, the first physico-chemical property comprises: (i) ion mobility; (ii) differential mobility; (iii) rate of change of ion mobility with electric field strength; and/or (iv) mass to charge ratio.

In an embodiment, the control system is arranged and adapted to control the operating environment within the separation device so as to maintain a substantially stable operating environment within the separation device.

In an embodiment, the control system is arranged and adapted to control the operating environment within the separation device so as to maintain a substantially stable operating environment within the separation device when the operating environment within or of one or more of the one or more first devices or stages changes or varies.

In an embodiment, the control system is arranged and adapted to control the operating environment within the separation device so as to avoid or reduce changes or variations in the operating environment within the separation device that would otherwise occur due to changes or variations in the operating environment within or of one or more of the one or more first devices or stages.

In an embodiment, the separation device is coupled to the one or more first devices or stages such that the operating environment within the separation device depends on the operating environment within or of one or more of the one or more first devices or stages.

In an embodiment, the separation device is coupled to the one or more first devices or stages such that the composition of one or more gases within the separation device depends on the operating environment within or of the one or more first devices or stages, and in an embodiment such that the composition of one or more gases within the separation device depends on the composition of one or more gases within or at the one or more first devices or stages.

In an embodiment, the separation device is coupled to the one or more first devices or stages such that the pressure within the separation device depends on the operating environment within or of the one or more first devices or stages, and in an embodiment such that the pressure within the separation device depends on the pressure within or at the one or more first devices or stages.

In an embodiment, the separation device is coupled to the one or more first devices or stages such that the separation device is provided or filled with gas from the one or more first devices or stages.

In an embodiment, the control system is arranged and adapted to monitor the operating environment within the separation device by monitoring the composition of one or more gases.

In an embodiment, the control system is arranged and adapted to monitor the operating environment within the separation device by monitoring one or more pressures.

In an embodiment, the control system is arranged and adapted to monitor the operating environment within the separation device:
by monitoring a total or absolute pressure; and/or
by monitoring a plurality of partial pressures.

In an embodiment, the control system is arranged and adapted to monitor the operating environment within the separation device by directly monitoring the operating environment within the separation device.

In an embodiment, the control system is arranged and adapted to monitor the operating environment within the separation device by indirectly monitoring the operating environment within the separation device.

In an embodiment, the control system is arranged and adapted to indirectly monitor the operating environment within the separation device:
by monitoring an operating environment within or of one or more of the one or more first devices or stages arranged upstream of the separation device; and/or by monitoring an operating environment within or of one or more of the one or more second devices or stages arranged downstream of the separation device; and/or
by monitoring an operating environment within or of one or more chambers coupled to the separation device.

In an embodiment, the one or more first devices or stages comprise an ion source.

In an embodiment, the ion source comprises an atmospheric ion source.

In an embodiment, the one or more first devices or stages comprises a liquid chromatography device optionally coupled to the ion source.

In an embodiment, the liquid chromatography device is upstream of the ion source.

In an embodiment, the one or more first devices or stages comprises one or more transfer regions optionally downstream of the ion source.

In an embodiment, the one or more first devices or stages comprises one or more traps or trap regions optionally downstream of the ion source and optionally downstream of the one or more transfer regions.

In an embodiment, the pressure within the separation device is less than the pressure within or at the one or more first devices or stages.

In an embodiment, the mass spectrometer further comprises one or more second devices or stages arranged downstream of the separation device.

In an embodiment, the one or more second devices or stages comprise a mass analyser.

In an embodiment, the pressure within the separation device is greater than the pressure within or at the one or more second devices or stages.

In an embodiment the separation device comprises a trap region and a separation or drift region; and
the control system is arranged and adapted to monitor the operating environment within the separation device by monitoring the trap region and/or the separation or drift region.

In an embodiment, the control system is arranged and adapted to monitor the operating environment within the separation device: (i) substantially continuously; (ii) non-continuously; and/or (ii) periodically.

In an embodiment, the control system is arranged and adapted to control the operating environment within the separation device by controlling the composition of one or more gases within the separation device.

In an embodiment, the control system is arranged and adapted to control the operating environment within the separation device by controlling one or more pressures within the separation device.

In an embodiment, the control system is arranged and adapted:

to control the total or absolute pressure within the separation device; and/or to control a plurality of partial pressures within the separation device.

In an embodiment, the control system is arranged and adapted to correct one or more measurements of drift time and/or collision cross section made by the mass spectrometer based on the monitoring.

According to an aspect there is provided a method of mass spectrometry comprising:

providing a separation device for separating ions according to a first physico-chemical property;

providing one or more first devices or stages upstream of the separation device;

monitoring directly or indirectly the operating environment within the separation device; and controlling the operating environment within the separation device based on the monitoring by controlling one or more gas flows to or within one or more of the one or more first devices or stages.

According to an aspect there is provided a method of mass spectrometry comprising:

providing a separation device for separating ions according to a first physico-chemical property;

providing one or more first devices or stages upstream of the separation device;

monitoring directly or indirectly the operating environment within the separation device; and correcting one or more measurements made using the mass spectrometer based on the monitoring when the operating environment within the separation device changes or varies due to changes or variations in the operating environment within or of one or more of the one or more first devices or stages.

According to an aspect there is provided a mass spectrometer comprising:

an ion mobility separator for separating ions according to their ion mobility; and a control system arranged and adapted:

(i) to monitor directly or indirectly an operating environment within the ion mobility separator.

According to an aspect there is provided a mass spectrometer comprising:

a separation device arranged and adapted to separate ions according to a first physico-chemical property; and a control system arranged and adapted:

(i) to monitor directly or indirectly an operating environment within the separation device.

According to an aspect there is provided a method of mass spectrometry comprising:

providing an ion mobility separator for separating ions according to their ion mobility; and monitoring directly or indirectly an operating environment within the ion mobility separator.

According to an aspect there is provided a method of mass spectrometry comprising:

providing a separation device for separating ions according to a first physico-chemical property; and monitoring directly or indirectly an operating environment within the separation device.

According to an aspect there is provided a method of and an apparatus for ion mobility-mass spectrometry comprising:

an ion mobility separation device wherein the operating environment of the ion mobility separation device is directly and/or indirectly monitored.

According to an embodiment the monitoring of the environment is used to directly control the environment so as to maintain a stable environment.

According to an embodiment the monitoring of the environment is used to correct drift time or collision cross section measurements made in the environment.

According to an embodiment the act of monitoring the environment includes monitoring the absolute pressure of the ion mobility environment.

According to an embodiment the act of monitoring the environment includes monitoring the partial pressure of one or more components in the ion mobility environment.

According to an embodiment the ion mobility separation device is coupled to a mass spectrometer or mass analyser.

According to an embodiment the ion mobility separation device is coupled to liquid chromatography system.

An embodiment improves the accuracy and precision of collision cross section measurements for ion mobility separation ("IMS") devices.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infra-red radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage optionally has an amplitude selected from the group consisting of: (i) about <50 V peak to peak; (ii) about 50-100 V peak to peak; (iii) about 100-150 V peak to peak; (iv) about 150-200 V peak to peak; (v) about 200-250 V peak to peak; (vi) about 250-300 V peak to peak; (vii) about 300-350 V peak to peak; (viii) about 350-400 V peak to peak; (ix) about 400-450 V peak to peak; (x) about 450-500 V peak to peak; and (xi) >about 500 V peak to peak.

The AC or RF voltage may have a frequency selected from the group consisting of: (i) <about 100 kHz; (ii) about 100-200 kHz; (iii) about 200-300 kHz; (iv) about 300-400 kHz; (v) about 400-500 kHz; (vi) about 0.5-1.0 MHz; (vii) about 1.0-1.5 MHz; (viii) about 1.5-2.0 MHz; (ix) about 2.0-2.5 MHz; (x) about 2.5-3.0 MHz; (xi) about 3.0-3.5 MHz; (xii) about 3.5-4.0 MHz; (xiii) about 4.0-4.5 MHz; (xiv) about 4.5-5.0 MHz; (xv) about 5.0-5.5 MHz; (xvi) about 5.5-6.0 MHz; (xvii) about 6.0-6.5 MHz; (xviii) about 6.5-7.0 MHz; (xix) about 7.0-7.5 MHz; (xx) about 7.5-8.0 MHz; (xxi) about 8.0-8.5 MHz; (xxii) about 8.5-9.0 MHz; (xxiii) about 9.0-9.5 MHz; (xxiv) about 9.5-10.0 MHz; and (xxv) >about 10.0 MHz.

The mass spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i) <about 0.0001 mbar; (ii) about 0.0001-0.001 mbar; (iii) about 0.001-0.01 mbar; (iv) about 0.01-0.1 mbar; (v) about 0.1-1 mbar; (vi) about 1-10 mbar; (vii) about 10-100 mbar; (viii) about 100-1000 mbar; and (ix) >about 1000 mbar.

According to an embodiment analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions may comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

According to an embodiment the process of Electron Transfer Dissociation fragmentation comprises interacting analyte ions with reagent ions, wherein the reagent ions comprise dicyanobenzene, 4-nitrotoluene or azulene.

BRIEF DESCRIPTION OF THE DRAWINGS

Various embodiments will now be described, by way of example only, and with reference to the accompanying drawings in which.

DETAILED DESCRIPTION

Various embodiment will now be described in more detail below.

Figure 1:
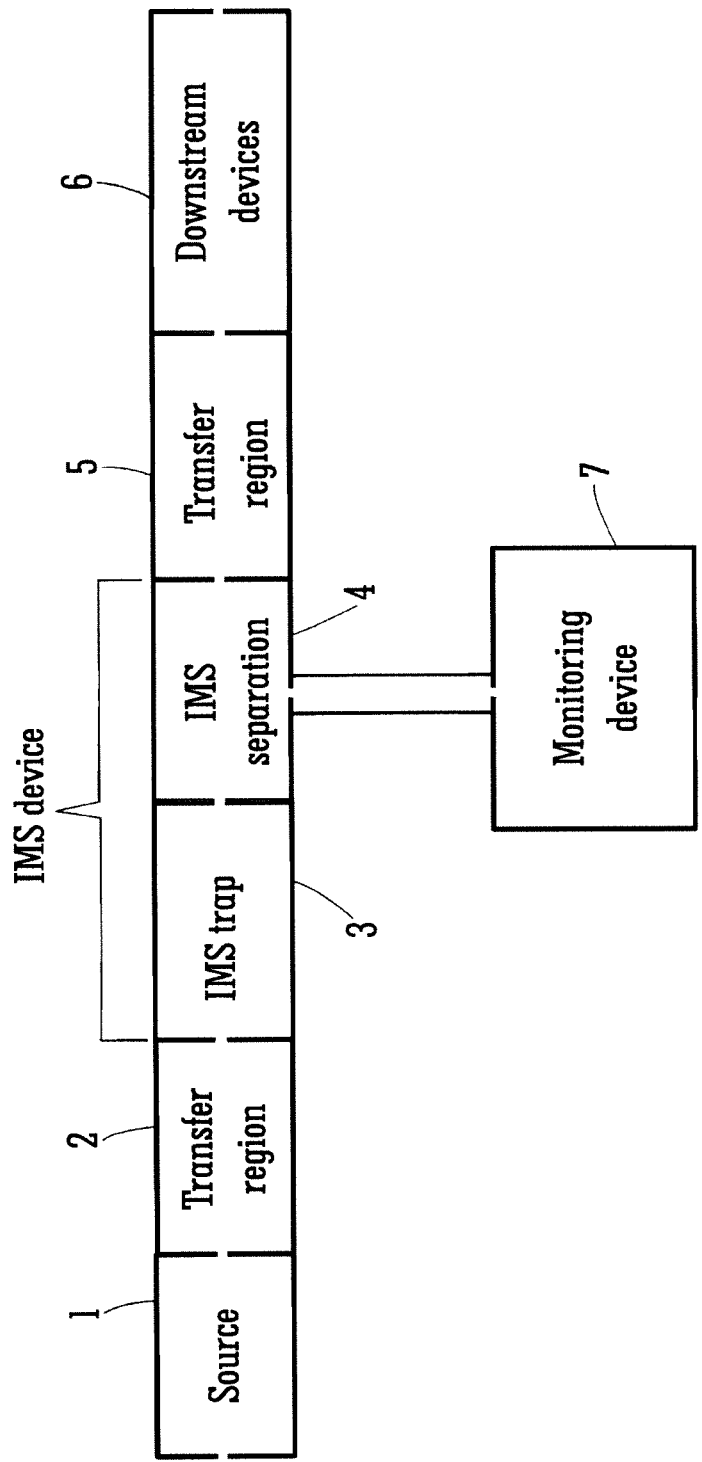
FIG. 1 shows an embodiment wherein the ion mobility separator environment is monitored directly.

FIG. 1 shows a mass spectrometer according to an embodiment. The mass spectrometer comprises an ion source 1, with a first ion transfer region 2 arranged downstream of the ion source 1. The ion source 1 may comprise an atmospheric pressure ion source.

An ion mobility separation device comprising a trap region 3 and an ion mobility separation region 4, is arranged downstream of the ion source 1 and the first transfer region 2. A second transfer region 5 is optionally arranged downstream of the ion mobility separation device, and one or more further downstream devices or stages 6 are optionally arranged downstream of the second transfer region 5.

The further downstream devices or stages 6 may comprise a mass analyser, mass filter and/or one or more other analytical devices. For example, the further downstream devices or stages 6 may comprise a Time of Flight ("ToF") mass analyser, one or more quadrupole mass filters, one or more ion traps, and/or one or more inductive detection based mass analysing traps (e.g. one or more Fourier Transform Ion Cyclotron Resonance ("FTICR") mass analysers and/or one or more electrostatic mass analysers arranged to generate an electrostatic field having a quadro-logarithmic potential distribution).

Thus, the ion mobility separation device is coupled between the ion source 1 and the one or more downstream devices 6. According to an embodiment the operating pressure of the ion mobility separation device is less than the operating pressure of the ion source 1 (e.g. less than atmospheric pressure) but greater than the operating pressure of the one or more downstream devices 6 (e.g. of the mass analyser).

This is advantageous in terms of cost and simplicity, as the mass spectrometer of An embodiment need not comprise one or more stages of differential pumping between the ion source 1 and the ion mobility separation device, and the ion mobility separation device need not be re-filled with a buffer gas.

In an embodiment, possible variations in the (internal) environment of the ion mobility separation device due to variations in the ambient environment (e.g. due to changes in the ambient environment due to liquid chromatography ("LC") gradient changes, changes in sample or matrix flow rates and/or changes in source gas flows rates) which can affect measurements made using the ion mobility separation device (e.g. ion mobility drift time measurements and/or collision cross section ("CCS") measurements) are addressed by monitoring the environment of the ion mobility separation device. The monitoring may be used to control the environment (i.e. to maintain the environment in a relatively stable state) and/or to correct measurements e.g. of ion mobility separation drift times, collision cross section values, etc.

Thus, an embodiment comprises a monitoring device 7 arranged and adapted to monitor the operating environment of the ion mobility separator.

The monitoring device 7 may be arranged and adapted either to monitor the ion mobility separator environment directly or indirectly. The monitoring device 7 may be arranged and adapted to monitor the ion mobility separation region 4 or the trapping region 3 of the ion mobility separator.

In the embodiment depicted in FIG. 1, the monitoring device 7 is arranged and adapted to directly monitor the ion mobility separation region 4 of the ion mobility separator.

Figure 2:
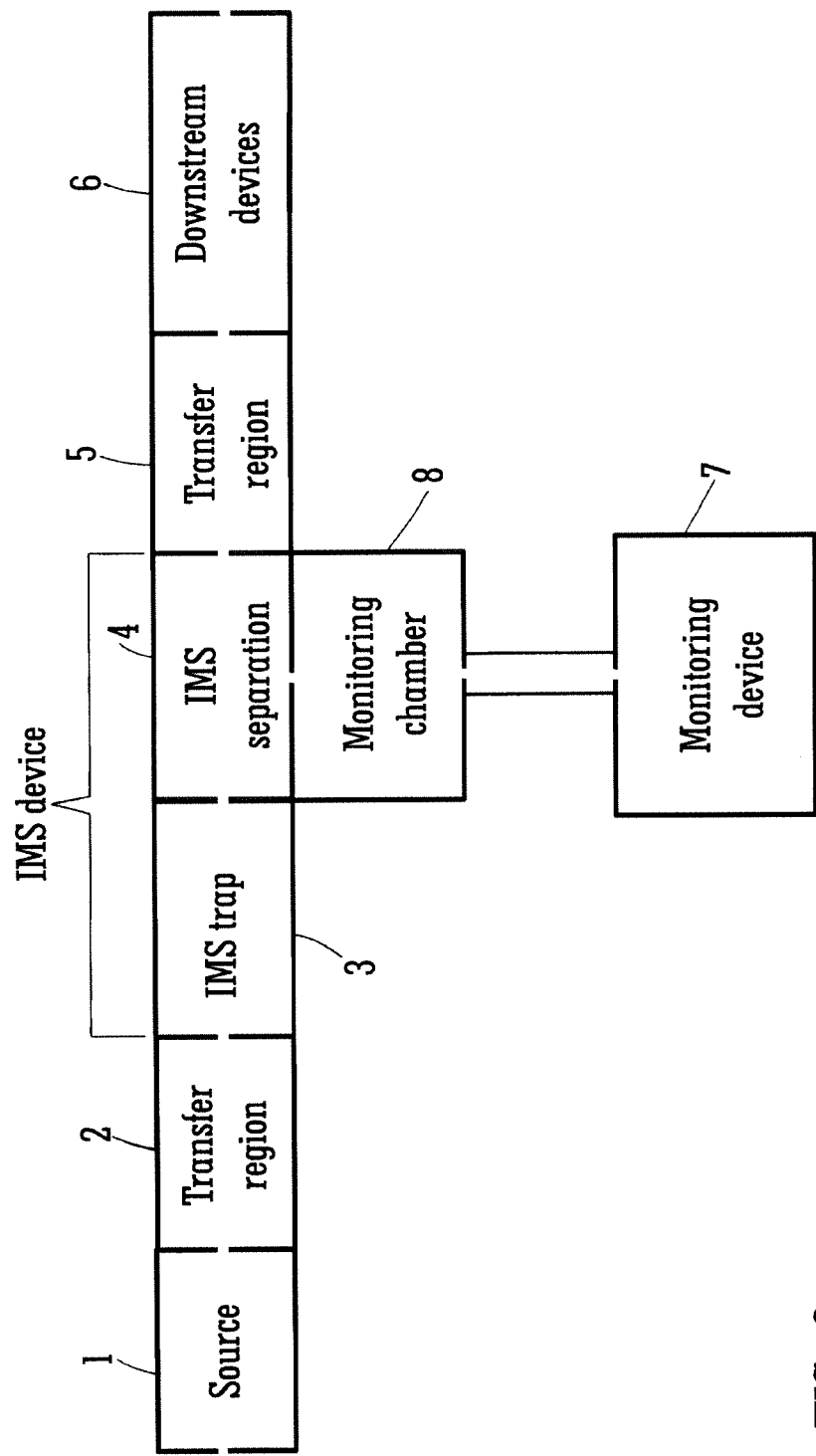
FIG. 2 shows an embodiment wherein the ion mobility separator environment is monitored indirectly.

FIG. 2 shows a mass spectrometer in accordance with another embodiment. The mass spectrometer depicted in FIG. 2 is similar to the mass spectrometer depicted in FIG. 1, except that the monitoring device 7 is arranged and adapted to monitor an additional monitoring chamber 8 which is in communication with the ion mobility separator, via the ion mobility separation region 4. In another embodiment, the monitoring chamber 8 and monitoring device 7 may be arranged in communication with the ion mobility trapping region 3. The monitoring chamber 8 is differentially pumped from the ion mobility separator.

Figure 3:
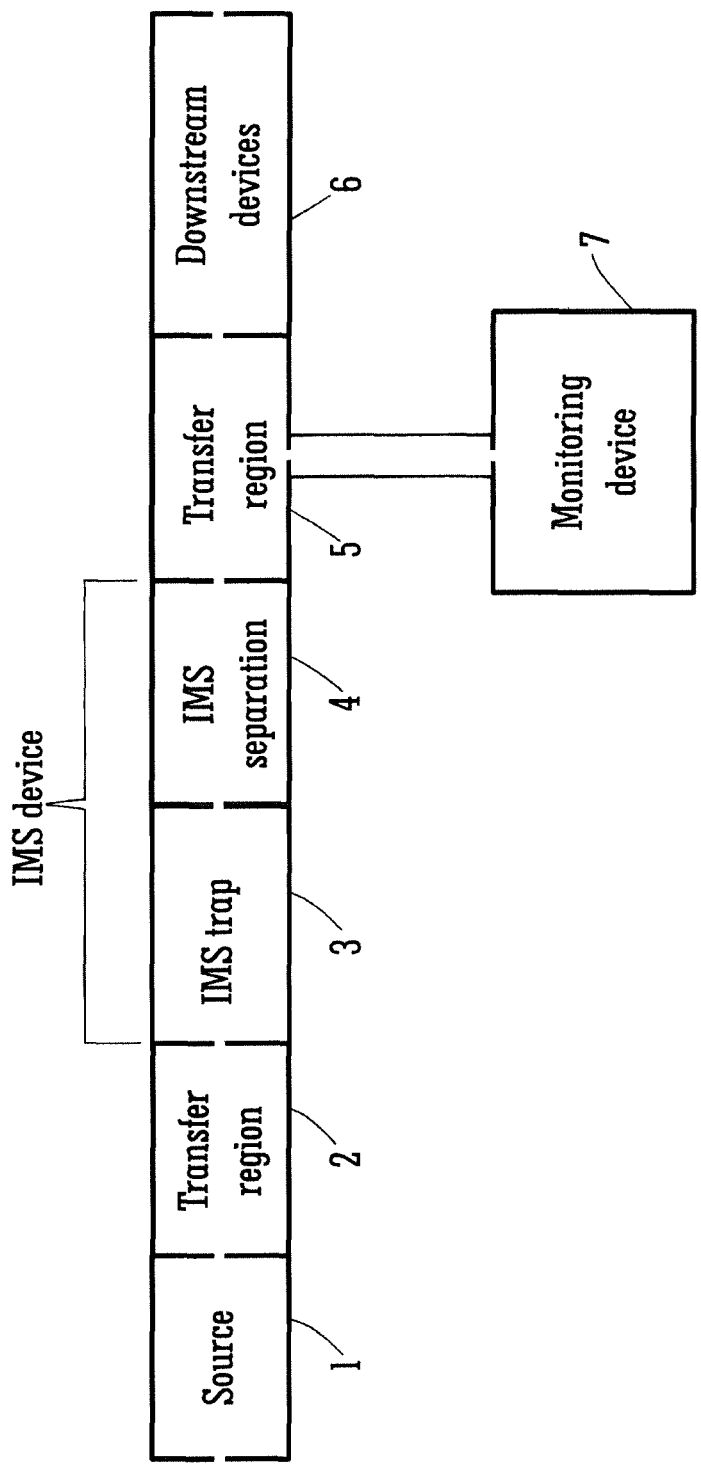
FIG. 3 shows an embodiment wherein the ion mobility separator environment is monitored indirectly.

FIG. 3 shows a mass spectrometer in accordance with another embodiment. The mass spectrometer depicted in FIG. 3 is similar to the mass spectrometer depicted in FIGS. 1 and 2, except that the monitoring device 7 is arranged and adapted to monitor a downstream chamber of the mass spectrometer that is already present in the instrument geometry. In particular, in FIG. 3 the monitoring device 7 may be arranged and adapted to monitor the second transfer region 5. In various other embodiments one or more upstream chambers, such as the first transfer region 2, may be monitored.

In one embodiment, the monitoring device 7 may comprise a vacuum gauge which provides a measurement of total or absolute pressure. Additionally or alternatively, the monitoring device 7 may comprise a more complex device, such as a residual gas analysis ("RGA") device that provides partial pressure measurements of the components making up the background gas and/or environment.

In one embodiment (which will be described in more detail with reference to FIG. 4), the measurements obtained from the monitoring of the environment may be used as part of a closed-loop feedback system, in conjunction with one or more mass flow controllers 10, 11, 12 (or equivalent devices), to maintain a constant environment within the ion mobility separator thereby effectively decoupling the environment in the ion mobility separator from changes in the ambient environment.

In one such embodiment, one or more mass flow controllers 10, 11, 12 are arranged and adapted to control one or more external gas sources so as to controllably introduce one or more gases into the ion mobility separation region 4, via one or more upstream stages of the mass spectrometer.

Figure 4:
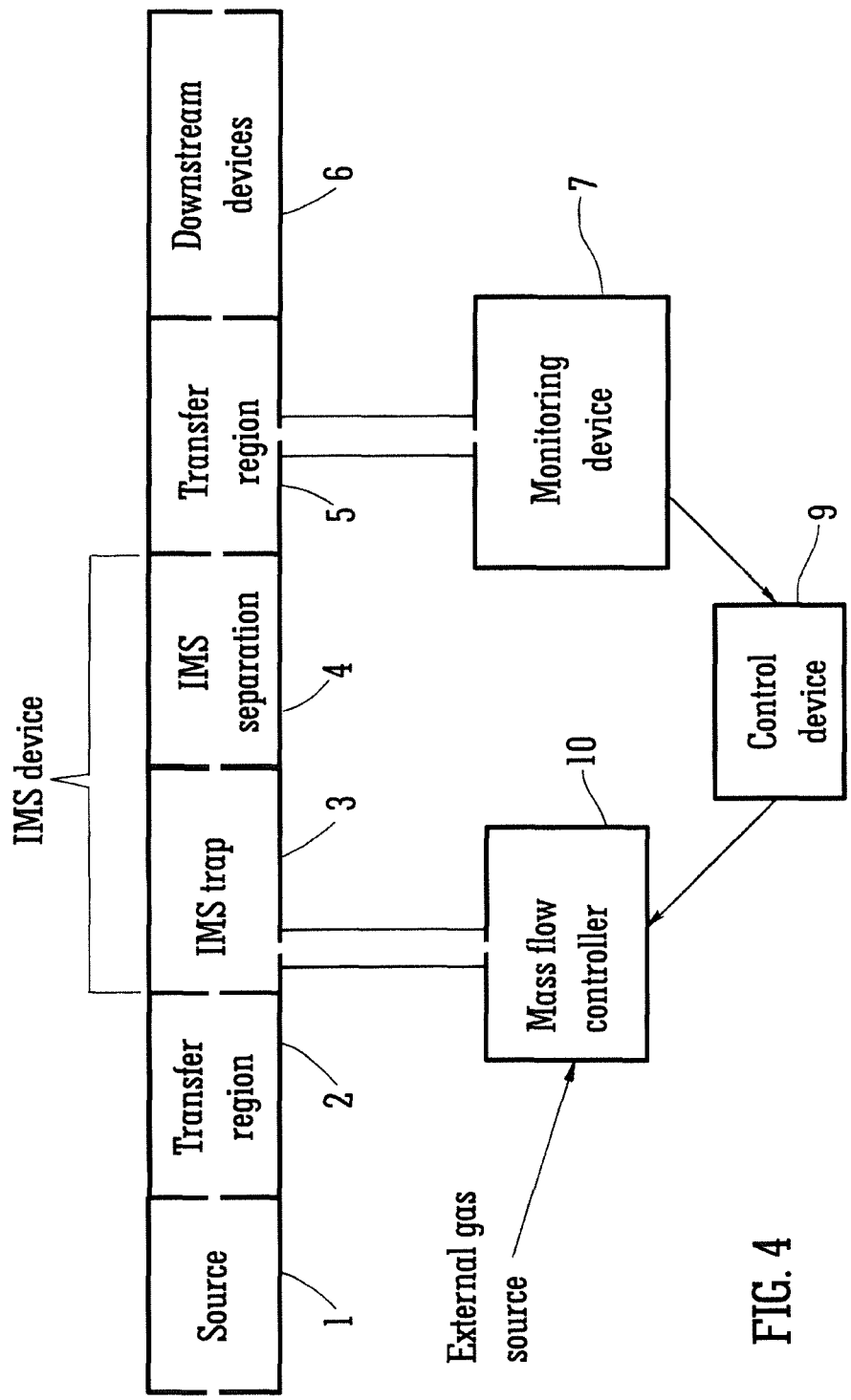
FIG. 4 shows an embodiment wherein a closed loop feedback system in conjunction with one or more mass controllers is used to maintain a constant environment.

FIG. 4 shows a mass spectrometer in accordance with an embodiment. The mass spectrometer depicted in FIG. 4 is similar to the mass spectrometer depicted in FIG. 3, in that the monitoring device 7 is shown monitoring the downstream transfer region 5. In other embodiments, the monitoring device 7 may be arranged to monitor other regions (as discussed above and as shown in FIGS. 1 and 2).

In the embodiment depicted in FIG. 4, the monitored values from the monitoring device 7 are used, via a control device 9, to control a mass flow controller 10. The mass flow controller 10 controls an external gas source so as to introduce one or more gases into the ion mobility separation region 4 via the trapping region 3, so as to maintain the environment within the ion mobility separation region 4 in a stable state.

FIG. 4 shows a single mass flow controller 10 controlling gas flowing into the ion mobility trapping region 3. In various other embodiments, one or more mass flow controllers 10, 11, 12 may control one or more gases flow into any devices and/or chambers upstream of the ion mobility separation region 4. In one such embodiment, a mass flow controller 10 may control gas flowing into the ion source 1.

Figure 5:
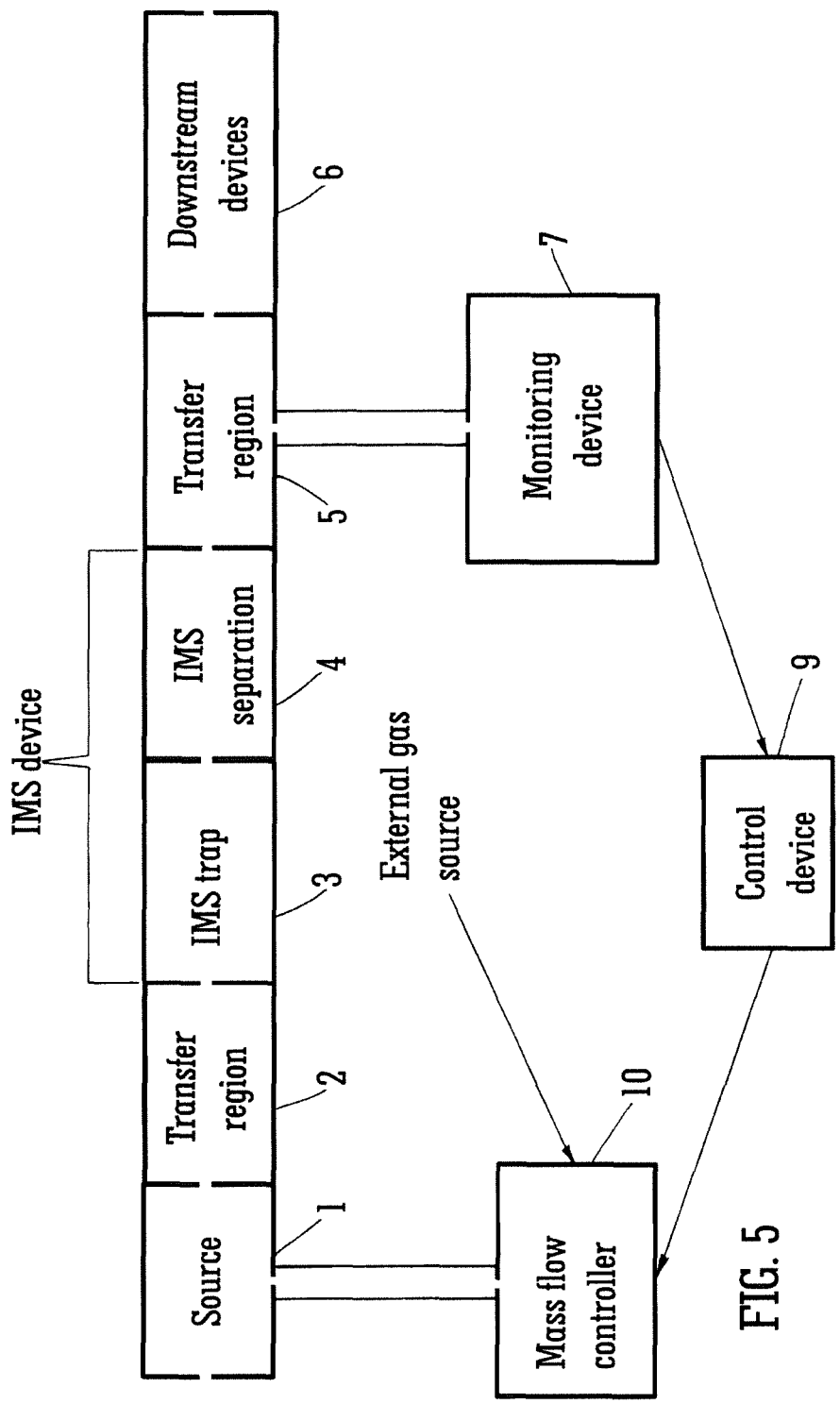
FIG. 5 shows an embodiment wherein a mass flow controller is used to control the ambient pressure source region.

FIG. 5 shows a mass spectrometer in accordance with an embodiment. The mass spectrometer depicted in FIG. 5 is similar to the mass spectrometer depicted in FIG. 4 except that the mass flow controller 10 controls gas flowing from an external gas source into the ion source region 1 which is an atmospheric pressure region.

Whilst FIGS. 4 and 5 illustrate the use of a single mass flow controller 10, further embodiments may utilise multiple mass flow controllers 10, 11, 12 controlling the flow of one or more different gases into one or more upstream devices or stages of the mass spectrometer. According to an embodiment the gases are ion mobility separator environment component gases.

Figure 6:
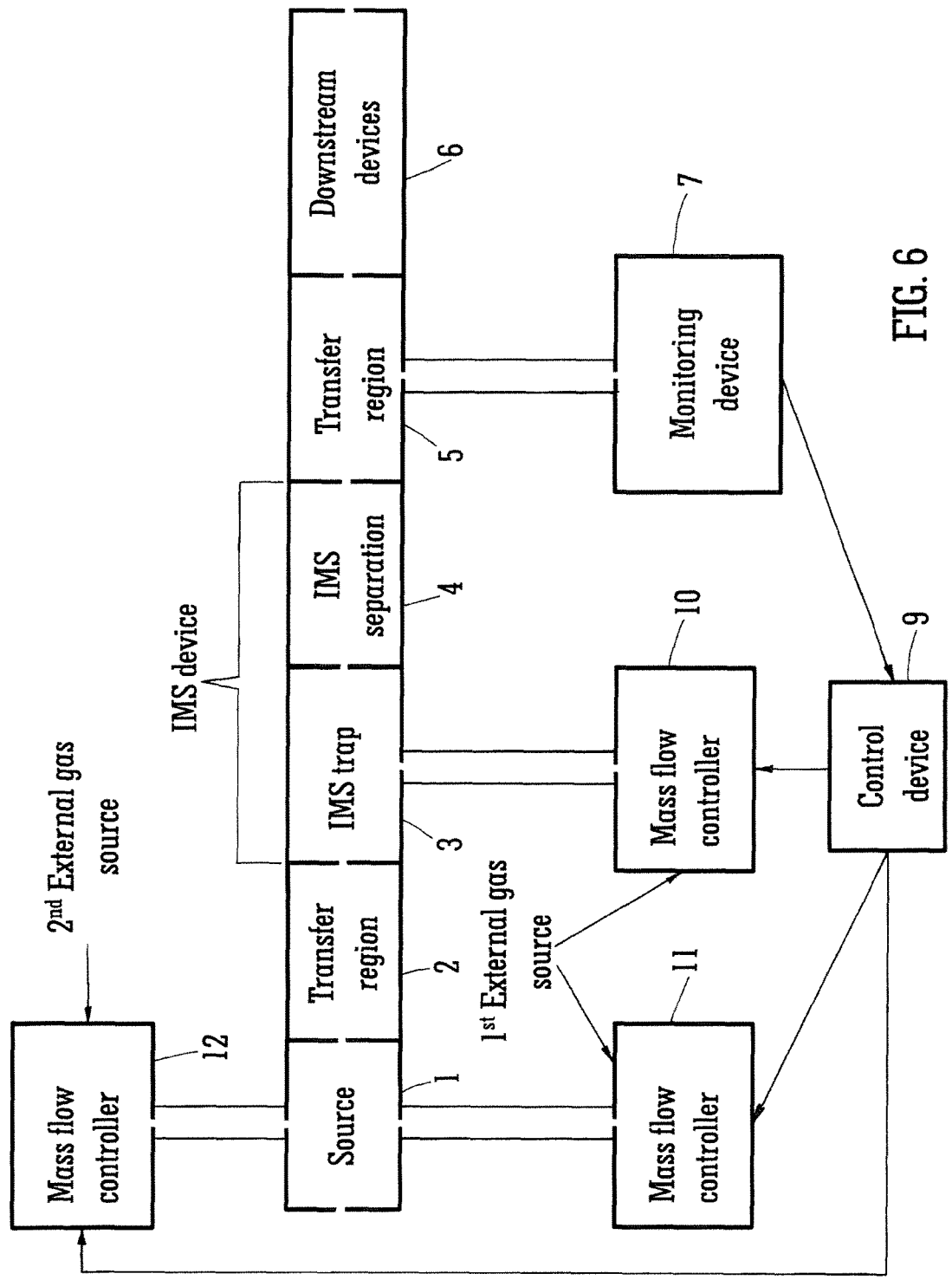
FIG. 6 shows an embodiment comprising multiple mass flow controllers.

FIG. 6 shows a mass spectrometer in accordance with an embodiment. The mass spectrometer depicted in FIG. 6 is similar to the mass spectrometer depicted in FIG. 5 except that multiple mass flow controllers 10, 11, 12 are used to control the flow of gases from two different external gas sources into two different upstream regions of the mass spectrometer. In particular, a first mass controller 10 controls the flow of a first gas into the ion mobility trapping region 3, a second mass flow controller 11 controls the flow of the first gas into the ion source 1, and a third mass flow controller 12 controls the flow of a second gas into the ion source 1.

In an alternative embodiment, the environment within the ion mobility separator is allowed to vary with the ambient environment, and the monitoring is used to provide data allowing for correction of measurements, e.g. of drift times or collision cross section. The measured values are then corrected e.g. in post-processing.

A wide range of mass analysers and ionisation sources may be used in conjunction with an embodiment.

The approach according to an embodiment may be applied to a wide range of separation devices including DC drift tube ion mobility separators, travelling wave ion mobility separators, differential mobility analysers, differential mobility spectrometers, and/or Field Asymmetric-Waveform Ion Mobility Separation ("FAIMS") devices.

The approach according to various embodiments may also be applied to other separation devices that separate ions according to any desired physico-chemical property e.g. which operate at elevated pressures wherein the pressure affects the elution or drift times of ions. Examples of such device are described in U.S. Pat. No. 7,919,747 (Micromass), U.S. Pat. No. 8,153,960 (Micromass) and U.S. Pat. No. 8,426,802 (Micromass), the contents of which are incorporated herein by reference. As will be appreciated by those having skill in the art, various embodiments may be used to improve the accuracy and/or precision of measurements made using such instruments.

The mass spectrometer according to various embodiments may be configured to operate in and may be operated in any mode of operation as desired. For example, analytical techniques utilising ion fragmentation or reaction and conformational changing devices may be performed in accordance with an embodiment.

In various embodiments, the monitoring may be continuous, effectively acting in real time, or can be periodic and discrete, operating with a time period short enough to sample significant environment changes. In another embodiment, the monitoring can be non-continuous and non-periodic, e.g. the environment can be monitored at irregular time intervals.

Although the present invention has been described with reference to preferred embodiments, it will be understood by those skilled in the art that various changes in form and detail may be made without departing from the scope of the invention as set forth in the accompanying claims.

The invention claimed is:

1. A mass spectrometer comprising:
an ion mobility separator for separating ions according to their ion mobility;
one or more first devices or stages comprising an ion source arranged upstream of said ion mobility separator;
a monitoring device configured to monitor directly or indirectly an operating environment within said ion mobility separator by monitoring one or more pressures; and
a flow controller configured to control one or more gas flows to or within one or more of said one or more first devices or stages upstream of said ion mobility separator;
wherein said mass spectrometer is configured to control said operating environment within said ion mobility separator based at least in part on the one or more pressures of said monitoring by controlling said one or more gas flows to or within one or more of said one or more first devices or stages so as to maintain a substantially stable operating environment within said ion mobility separator; and
wherein the pressure within said ion mobility separator is less than the pressure within or at said one or more first devices or stages.

2. A mass spectrometer as claimed in claim 1, wherein said ion mobility separator is coupled to said one or more first devices or stages such that the operating environment within said ion mobility separator depends on the operating environment within or of one or more of said one or more first devices or stages.

3. A mass spectrometer as claimed in claim 1, wherein said ion mobility separator is coupled to said one or more first devices or stages such that the composition of one or more gases within said ion mobility separator depends on the operating environment within or of one of said one or more first devices or stages.

4. A mass spectrometer as claimed in claim 1, wherein said ion mobility separator is coupled to said one or more first devices or stages such that the pressure within said ion mobility separator depends on the operating environment within or of one of said one or more first devices or stages.

5. A mass spectrometer as claimed in claim 1, wherein said ion mobility separator is coupled to said one or more first devices or stages such that said ion mobility separator is provided or filled with gas from said one or more first devices or stages.

6. A mass spectrometer as claimed in claim 1, wherein said one or more first devices or stages comprises an ion, a liquid chromatography device, one or more transfer regions, and/or one or more traps or trap regions.

7. A mass spectrometer as claimed in claim 1, further comprising one or more second devices or stages arranged downstream of said ion mobility separator, wherein said one or more second devices or stages comprises a mass analyser.

8. A mass spectrometer as claimed in claim 7, wherein the pressure within said ion mobility separator is greater than the pressure within or at said one or more second devices or stages.

9. A method of mass spectrometry comprising:
providing an ion mobility separator for separating ions according to their ion mobility;
providing one or more first devices or stages comprising an ion source upstream of said ion mobility separator;
monitoring directly or indirectly said operating environment within said ion mobility separator by monitoring one or more pressures; and
controlling said operating environment within said ion mobility separator based at least in part on the one or more pressures of said monitoring by controlling one or more gas flows to or within one or more of said one or more first devices or stages so as to maintain a substantially stable operating environment within said ion mobility separator;
wherein the pressure within said ion mobility separator is less than the pressure within or at said one or more first devices or stages.

10. A method as claimed in claim 9, comprising controlling said operating environment within said ion mobility separator so as to maintain a substantially stable operating environment within said ion mobility separator when said operating environment within or of one or more of said one or more first devices or stages changes or varies.

11. A method as claimed in claim 9, comprising controlling said operating environment within said ion mobility separator so as to avoid or reduce changes or variations in said operating environment within said ion mobility separator that would otherwise occur due to changes or variations in said operating environment within or of one or more of said one or more first devices or stages.

12. A method as claimed in claim 9, comprising monitoring directly or indirectly said operating environment within said ion mobility separator by monitoring the composition of one or more gases.

13. A method as claimed in claim 9, comprising monitoring indirectly said operating environment within said ion mobility separator:
by directly monitoring an operating environment within or of one or more of said one or more first devices or stages arranged upstream of said ion mobility separator; and/or
by directly monitoring an operating environment within or of one or more second devices or stages arranged downstream of said ion mobility separator; and/or by directly monitoring an operating environment within or of one or more chambers coupled to said ion mobility separator.

14. A method as claimed in claim 9, comprising controlling said operating environment within said ion mobility separator by controlling the composition of one or more gases within said ion mobility separator.

15. A method as claimed in claim 9, comprising controlling said operating environment within said ion mobility separator by controlling one or more pressures within said ion mobility separator.

16. A mass spectrometer comprising:
an ion mobility separator for separating ions according to their ion mobility;
one or more first devices or stages comprising an ion source arranged upstream of said ion mobility separator; and
monitoring device configured to monitor directly or indirectly an operating environment within said ion mobility separator by monitoring one or more pressures;
wherein said ion mobility separator is coupled to said one or more first devices or stages such that the operating environment within said ion mobility separator depends on the operating environment within or of one or more of said one or more first devices or stages; and
wherein said mass spectrometer is configured to correct one or more measurements of drift time and/or collision cross section made using said mass spectrometer based at least in part on the one or more pressures of said monitoring when said operating environment within said ion mobility separator changes or varies due to changes or variations in the operating environment within or of one or more of said one or more first devices or stages.

17. A method of mass spectrometry comprising:
providing an ion mobility separator for separating ions according to their ion mobility;
providing one or more first devices or stages comprising an ion source upstream of said ion mobility separator;
monitoring directly or indirectly said operating environment within said ion mobility separator by monitoring one or more pressures; and
correcting one or more measurements of drift time and/or collision cross section made using said mass spectrometer based on said monitoring when said operating environment within said ion mobility separator changes or varies due to changes or variations in the operating environment within or of one or more of said one or more first devices or stages.

18. A mass spectrometer comprising:
an ion mobility separator for separating ions according to their ion mobility; one or more first devices or stages comprising an ion source arranged upstream of said ion mobility separator;
one or more second devices or stages arranged downstream of said ion mobility separator, wherein said one or more second devices or stages comprises a mass analyser; a monitoring device configured to monitor directly or indirectly an operating environment within said ion mobility separator by monitoring one or more pressures; and
a flow controller configured to control one or more gas flows to or within one or more of said one or more first devices or stages upstream of said ion mobility separator;
wherein said mass spectrometer is configured to control said operating environment within said ion mobility separator based on said monitoring by controlling said one or more gas flows to or within one or more of said one or more first devices or stages so as to maintain a substantially stable operating environment within said ion mobility separator; and
wherein the pressure within said ion mobility separator is greater than the pressure within or at said one or more second devices or stages.

* * * * *